(12) United States Patent  
Leung et al.

(10) Patent No.: US 8,961,537 B2
(45) Date of Patent: Feb. 24, 2015

(54) SURGICAL ROBOT WITH HYBRID PASSIVE/ACTIVE CONTROL

(75) Inventors: Kwok-sui Leung, Shatin (HK); Shao-Long Kuang, Shantin (HK); Yu Wang, Beijing (CN); Chun-sing Chui, Shatin (HK); Wing-Hoi Cheung, Shatin (HK); Pak-Leung Tsang, Tseung Kwan O (HK); Wai-kin Ng, Tai Po (HK)

(73) Assignees: The Chinese University of Hong Kong, Shatin, NT. (HK); Beihang University, Beijing (CN)

( * ) Notice: Subject to any disclaimer, the term of this patent is extended or adjusted under 35 U.S.C. 154(b) by 341 days.

(21) Appl. No.: 13/216,525

(22) Filed: Aug. 24, 2011

(65) Prior Publication Data

US 2013/0053866 A1    Feb. 28, 2013

(51) Int. Cl.
*A61B 19/00* (2006.01)
*B25J 9/16* (2006.01)
*B25J 17/00* (2006.01)
*B25J 18/00* (2006.01)
(Continued)

(52) U.S. Cl.
CPC ........... *B25J 9/1689* (2013.01); *A61B 19/2203* (2013.01); *B25J 18/005* (2013.01); *B25J 9/06* (2013.01); *B25J 19/0004* (2013.01); *G05B 2219/39212* (2013.01); *G05B 2219/39439* (2013.01); *G05B 2219/40415* (2013.01); *A61B 2019/2234* (2013.01); *Y10S 901/28* (2013.01); *Y10S 901/23* (2013.01)
USPC .......... 606/130; 74/490.03; 700/245; 901/28; 901/23

(58) Field of Classification Search
CPC .... A61B 19/00; A61B 19/2203; A61B 19/22; A61B 19/26; A61B 2017/00477; A61B 2019/2234; G05B 2219/39212; G05B 2219/39439; G05B 2219/40415; B25J 9/1689; B25J 9/06; B25J 19/0004; B25J 18/005
USPC ......................................... 901/28; 74/490.01
See application file for complete search history.

(56) References Cited

U.S. PATENT DOCUMENTS 5,337,732 A    8/1994  Grundfest et al.
6,050,530 A *  4/2000  Nakamura ................. 248/123.2

(Continued)

FOREIGN PATENT DOCUMENTS

CN    1328018 C     7/2007
CN    101357075 A   2/2009

(Continued)

OTHER PUBLICATIONS

Schafer, Ingolf and Slatter Rolf. "Precision pointing and actuation systems for UAVS using harmonic drive gears", Limburg, Germany. 2003 [ca]. 8 p.*

(Continued)

*Primary Examiner* — Gary Jackson
*Assistant Examiner* — Scott T. Luan
(74) *Attorney, Agent, or Firm* — Kilpatrick Townsend & Stockton LLP

(57) ABSTRACT

A surgical robot with seven degrees of freedom, including various types of joints, offers a hybrid active-passive control for operation both manually and by programmed navigation. One of the degrees of freedom allows the robot to be moved efficiently around the axis of a patient's body to provide ample workspace for surgical procedures in an operating room.

20 Claims, 5 Drawing Sheets

(51) Int. Cl.
*B25J 9/06* (2006.01)
*B25J 19/00* (2006.01)

(56) References Cited

U.S. PATENT DOCUMENTS

| | | | |
|---|---|---|---|
| 2005/0166413 A1* | 8/2005 | Crampton | 33/503 |
| 2007/0013336 A1* | 1/2007 | Nowlin et al. | 318/568.21 |
| 2007/0059032 A1* | 3/2007 | Yamada et al. | 399/107 |
| 2007/0265527 A1 | 11/2007 | Wohlgemuth | |
| 2009/0041565 A1* | 2/2009 | Rodriguez Y Baena | 414/431 |
| 2010/0300230 A1* | 12/2010 | Helmer | 74/469 |
| 2011/0282357 A1* | 11/2011 | Rogers et al. | 606/130 |
| 2012/0227531 A1* | 9/2012 | Subramanian et al. | 74/490.01 |

FOREIGN PATENT DOCUMENTS

| | | |
|---|---|---|
| CN | 201299596 Y | 9/2009 |
| CN | 100560304 C | 11/2009 |
| EP | 1854425 A1 | 11/2007 |
| JP | 2006218563 A | 8/2006 |

OTHER PUBLICATIONS

International Search Report in PCT Application No. PCT/CN2012/080579 mailed Dec. 6, 2012, 4 pages.

* cited by examiner

SURGICAL ROBOT WITH HYBRID PASSIVE/ACTIVE CONTROL

BACKGROUND OF THE INVENTION

1. Field of the Invention

This present invention relates to surgical robots and particularly to control methods for operating such robots.

2. Description of the Prior Art

Robotic systems have been used in clinical practice for over twenty years, during which time much progress has been made in the theory, technique and clinical applications of surgical robotics. While the robots initially used for surgical applications were industrial robots, dedicated robots have since been developed that are specifically designed to meet the specialized needs of surgery.

Industrial robots are designed for use in a structured environment, i.e., one in which every element is fixed. Such robots thus perform pre-programmed tasks repeatedly, without allowing for human intervention. The environment in a surgical operation, by contrast, is totally unstructured because body sizes differ among different patients, and because different operations tend to involve different and complex procedures. A surgical robot must be adaptable to these differences, and surgeons and their medical staffs must be able to intervene with and work closely with the robot. To adapt to the unique requirements of surgical operations, a surgical robot should thus be adaptable to different patients and different procedures and should be able to complement human abilities and trained skills. A surgical robot must also consume as small a space in an operating room as possible in order to minimize interference with the medical staff.

Medical Robotics of Stockholm, Sweden (http://www.medicalrobotics.se), supplies a surgical robot under the name "PinTrace" for use in orthopaedic surgery. This robot has an anthropomorphic structure with six revolute joints to provide a big workspace. Mazor Robotics Ltd. of Israel (http://www.mazorrobotics.com) supplies a surgical robot called "SpineAssist" for use in minimally invasive spine surgery. This is a miniature parallel robot with six degrees of freedom which is mounted on the spine during the surgery.

Control of a surgical robot is important in providing the robot with both utility and safety. Typical robotic systems have one of three control modes. The first is a passive control in which the robot is operated manually. The second is an active control in which the robot can move autonomously according to a pre-programmed trajectory. The third one is a tele-operation mode, in which the robot is controlled in real-time in response to on-line direct orders from the operator.

The TIMC Laboratory (France) (http://www-timc.imag.fr) offers a robot arm named "PADyC" for Cardiac Surgery Applications. This robot operates as a passive guide with dynamic constraints which limit the instrument motions according to a pre-defined surgical plan. Curexo Technology (Fremont, Calif., USA) offers the "ROBODOC" system for joint replacement surgery. This system can cut bone automatically, but the interaction between cutting tools and patient is controlled only by computer. Intuitive Surgical, Inc. (Sunnyvale, Calif., USA) (http://www.intuitivesurgical.com), offers a surgical robot for endoscopic surgery under the name "Da Vinci." This robot has three to four robot arms, and the surgeon can control these robot arms through tele-operation controllers.

SUMMARY OF THE INVENTION

The present invention resides in a surgical robot in which a tool holder is mounted to a base through linking members arranged in series, with joints connecting the linking members. The joints, which include an arc-shaped sliding joint that provides a suitable work space for surgical applications in an operating room, provide at least seven degrees of freedom. The invention also resides in a method for controlling the surgical robot by a hybrid control that includes both active and passive control modes, to provide enhanced control over the precision, utility, and safety of the surgical tool held in the tool holder.

Many surgical procedures involve movement in a linear direction, such as drilling or manipulating an instrument within the human body structure. Such procedures require only five degrees of freedom. The present invention provides two additional degrees of freedom and thereby presents a greater ability to avoid obstacles. One of the degrees of freedom is provided by a prismatic joint, which fulfills the function of motion through a linear path. Another degree of freedom is provided by an arc-shaped sliding joint, which provides motion along a fixed curve, similar to that of a revolute joint with a remote axis. The remaining degrees of freedom are supplied by revolute joints which revolve around fixed axes.

DETAILED DESCRIPTION OF THE INVENTION AND SELECTED EMBODIMENTS

Figure 1:
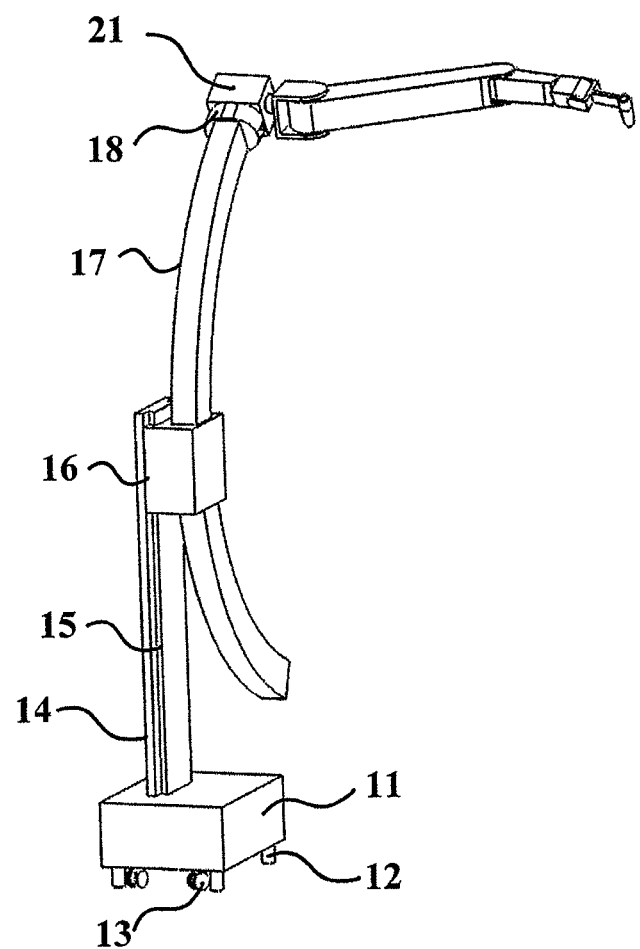
FIG. 1 is a schematic drawing of one example of a surgical robot in accordance with the present invention.

The term "prismatic joint" is used herein to denote a sliding joint that has only one degree of translation, typically in a linear direction, without allowing rotation of one part relative to another. The term "arc-shaped sliding joint" is used herein to denote a sliding joint in which the movement of one part follows an arc or a fixed curve, rather than a straight line. The typical arc-shaped sliding joint is one with a curved beam and a mating member that engages the beam such that the beam can slide within or along the mating member. The arc-shaped sliding joint is thus a form of prismatic joint since it does not allow rotation of the curved beam around an axis that is tangential to the curve of the beam. The term "revolute joint" is used herein to denote a joint with rotational motion around a single axis and no sliding motion. Each of the joints cited in this paragraph have but a single degree of freedom, although two or more joints together can provide multiple degrees of freedom.

In certain embodiments of the invention, the motion path of the prismatic joint is vertical, i.e., perpendicular to the ground, and the motion plane of the arc-shaped sliding joint is parallel with the motion path of the prismatic joint. The joints other than the prismatic and arc-shaped joints are revolute joints. The first revolute joint has an axis perpendicular to the motion plane of the second joint, and the second and third revolute joints have axes that are parallel to each other and perpendicular to the axis of the first revolute joint. The axis of the fourth revolute joint is perpendicular to the axis of the third revolute joint, and the axis of the fifth revolute joint is perpendicular to the axis of the fourth. And the fourth and fifth revolute joints have the same center of rotation, thereby collectively providing orientation adjustment around the center of a sphere.

The structure can be divided into two parts: a base with two degrees of freedom and a robot arm with five degrees of freedom. The first two joints form the base, and the prismatic joint can be used to adjust the height of the robot arm to accommodate operation tables of different heights. The arc-shaped sliding joint can then be used to adjust the position of the robot arm around the axis of the patient's body. The five revolute joints supply the five degrees of freedom to the robot arm, thereby providing sufficient dexterity for most surgical procedures.

Considering the human body as a cylinder, the arc-shaped sliding joint can bring the robot arm around the axis of the body, and thereby provide the most suitable work space for surgical procedures in the operating room. The arc-shaped sliding joint has the dexterity of a revolute joint plus a slide rail which provides it with the rigidity of the prismatic joint. The five revolute joints are motor-driven, for example by DC servo motors, and each one can also contain an optical encoder, a harmonic reducer, and an electromagnetic brake. Each joint therefore offers active-passive hybrid control, which means that the revolute joints can be driven both by electric power and manually.

The control mode change between the active mode and passive mode of any individual motor can be achieved by changing the power status of the motor. When the motor is powered, the holding torque of the motor will lock the joint, and the joint can operate under an active control mode driven by electric power. When power is no longer supplied to the motor, the joint can be operated manually under the passive control mode. In both the active and passive control modes, the movement of the joint can be monitored by an optical encoder, and the joint can be freely changed from active mode to passive mode and vice versa. An electromagnetic brake that is engaged when overload of the robotic system is detected provides extra holding torque to ensure the safety of the robot system.

In a surgical operation, a surgeon can move the robot arm to place the tool in a rough or approximate position, i.e., one that is near to, but not precisely at, the desired position, by operation of the robotic system in the passive control mode. The surgeon can then switch the robot to operate under active control in which fine adjustment can be performed to place the tool in its final position. This active-passive hybrid control method can shorten the operation time, minimize the range of automated motion, increase safety, and also ensure the precision and accuracy of the surgical operation.

Alternatively, the robot can be placed in an initial pose that is pre-programmed in accordance with a specific surgical operation and a specified workstation or operating room layout. It is known in the art that different surgical procedures will receive optimal performance when the surgical tool is positioned in a particular location, including position and orientation relative to the patient. Likewise, a given workspace will present certain issues such as accessibility to the patient and the need to accommodate supporting materials, equipment, or personnel. All of these factors can be included in determining the optimal initial pose for a procedure, and for any such procedure the optimal pose can be programmed into a surgical navigation system such that the robot can be automatically placed in or guided into such a position prior to the start of the operation. Fine-tuning can then be achieved by further automated movement or under visual guidance or position feedback.

Surgical navigation systems for use in the preceding paragraph are known in the art. Such systems utilize optical tracking, electromagnetic tracking, or other tracking methodologies. Tracking can entail either two-dimensional or three-dimensional image viewing from tracking devices located at the tool holder. Examples of tracking devices are light emitting diodes, ultrasonic emitters, and electromagnetic field emitters. Position feedback from a tracking device can be achieved by a computer display showing an image of the tool overlying an image of the patient or the surgical region on the patient.

The efficiency of a surgical robot is also a concern for surgeons. Robotic surgeries of the prior art tend to entail high costs in teens of time and personnel in placing the robotic system in a suitable position before surgery. With robotic systems of the present invention, the initial positions for different surgeries are planned pre-operatively. The robot can therefore be automatically placed in or guided into certain positions and orientations which are specific to the needs of different surgeries. The result is a significant decrease in setup time.

While the invention is susceptible to a wide range of implementations and embodiments, a full understanding of the novel features will be gained from an examination of a particular example. Such an example is shown in the attached drawings and described below.

Figure 2:
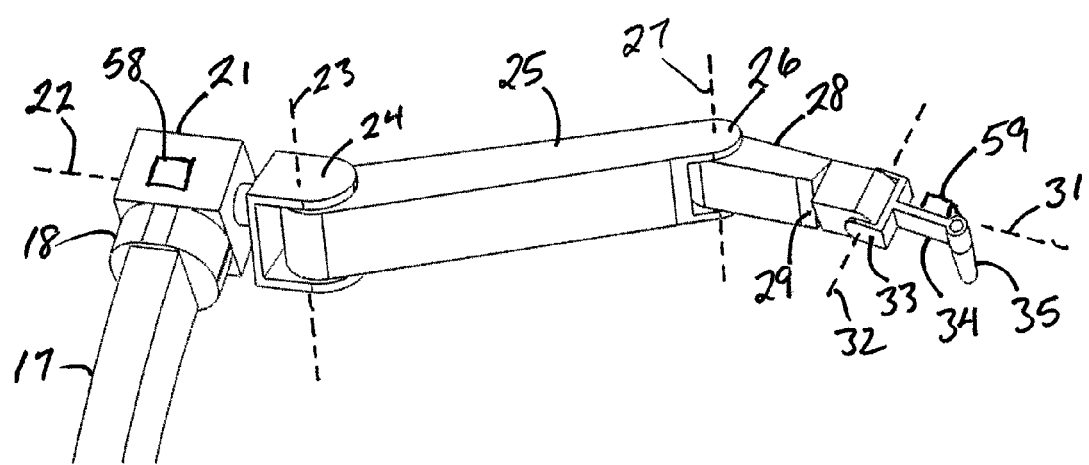
FIG. 2 is a schematic drawing of a portion of the surgical robot of FIG. 1.

FIGS. 1 and 2 schematically show a robot that supported by a block 11. The block 11 has four feet 12 that contact the floor of the operating room, plus three wheels 13 that are used to move the robot when the feet 12 are raised. The first joint is a prismatic joint that consists of a post 14 with a vertical slide rail 15 and a sliding block 16 that slides along the slide rail 15 to adjust the height of the robot arm which are the sections above the post and are discussed below. The second joint is an arc-shaped sliding joint that includes a curved passage through the same sliding block 16 plus an arc-shaped beam 17 that passes through the curved passage. The beam 17 can thus move along a fixed curve to which the center line of the sliding block 16 is tangent. At the top end of the arc-shaped beam 17 is a manually adjustable rotary joint 18 that allows manual rotation of robot arm over a range of at least 180°. With this rotary joint, the robot arm is easily positioned for use at both sides of the operating table.

The first revolute joint 21 is coupled to the rotary joint 18. The axis 22 of this first revolute joint (shown in FIG. 2) remains parallel to the floor of the operating room, and perpendicular to the axis 23 of the second revolute joint 24 which is coupled to the second first joint 21. The axis 23 of the second revolute joint intersects with the axis 22 of the first revolute joint. A linking member defined herein as an upper arm link 25 has one end coupled to the second revolute joint 24 and another end coupled to the third revolute joint 26. The axis 23 of the second revolute joint 24 is parallel to the axis 27 of the third revolute joint 26. A linking member defined herein as a lower arm link 28 is coupled at one end to the third revolute joint 26 and at the other end to the fourth revolute joint 29. The upper arm link 25 and the lower arm link 28 move in the same plane. The fourth revolute joint 29 has an axis 31 that is perpendicular to the axis 27 of the third revolute joint 26 and that intersects with the axis 32 of the fifth revolute joint 33. The fifth revolute joint 33 is coupled to the fourth revolute joint 31, and the axes of these two joints intersect. A linking member defined herein as a hand link 34 is coupled to the fifth revolute joint 33. At the tip of the hand link 34 is the tool holder 35 for a tool such as a drill sleeve or other medical instrument.

Figures 3A, 3B:
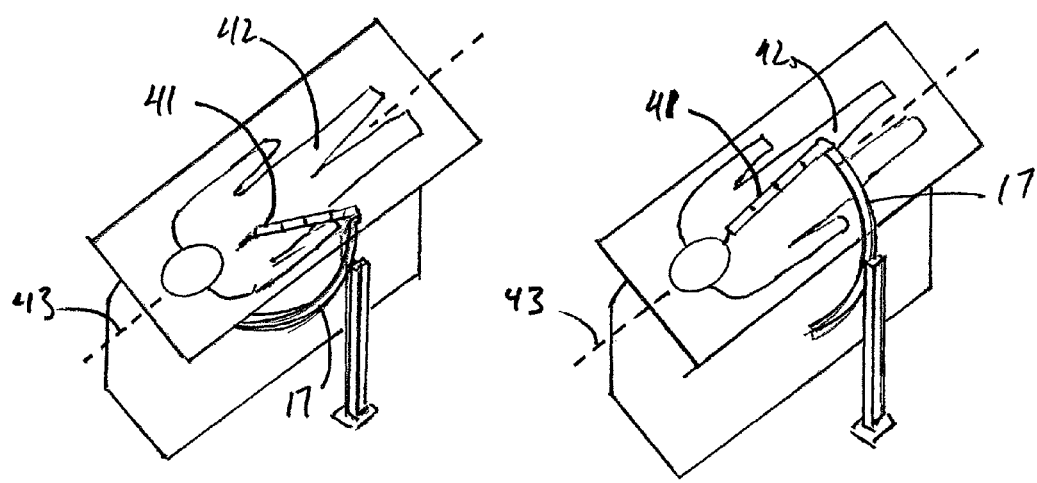
FIGS. 3A, 3B, and 3C illustrate three positions, respectively, of the arc-shaped sliding joint of the robot of FIG. 1, demonstrating the movement of the robot arm around the human body.
Figure 3C:
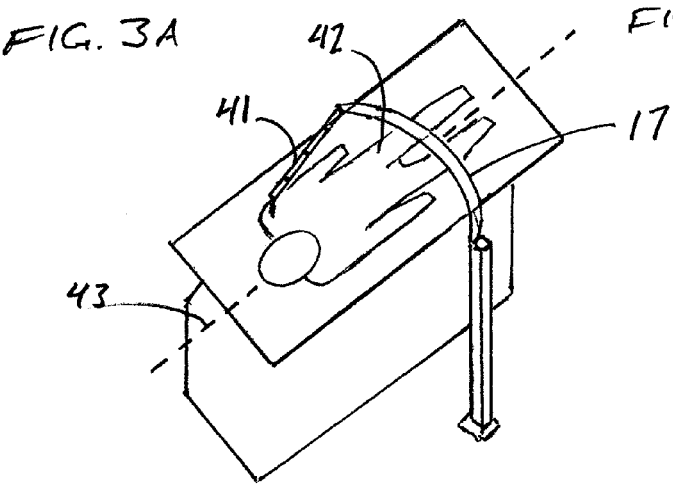

With the arc-shaped sliding joint formed by the block 16 and the arc-shaped beam 17, the robot arm, which term denotes all components from the first revolute joint 21 to the tool holder 35, can move around the axis of the patient's body, and thereby provide the most suitable work space for surgical procedure in the operating room. FIGS. 3A, 3B, and 3C show three different positions of the robot arm 41 relative to the patient's body 42, resulting from three different degrees of extension of the arc-shaped beam 17 around the axis 43 of the patient's body.

Figure 4:
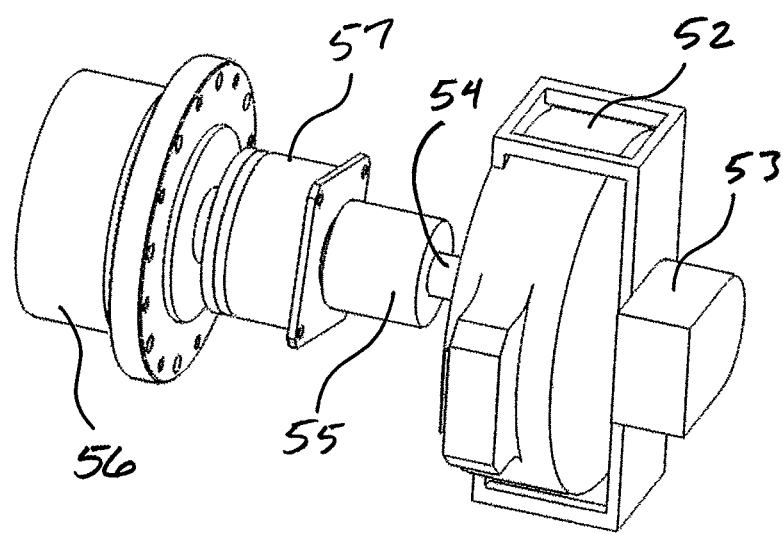
FIG. 4 is a schematic drawing of one example of a motor-driven revolute joint for an active-passive hybrid control according to the invention.

FIG. 4 depicts an example of a revolute joint 51 that can operate under both active and passive control. The joint is driven by a DC servo motor 52. An optical encoder 53 monitors the movement of the DC servo motor 52. The output shaft 54 of the DC servo motor is coupled to the shaft of the revolute joint by a coupling 55. The shaft of the revolute joint is linked to a harmonic reducer 56 to provide torque output. An electromagnetic brake 57 seizes the joint shaft in an emergency, such as when the robot arm experiences overload, to prevent the shaft from moving in any direction.

When the DC servo motor 52 is powered, the holding torque of the motor will lock the joint 51, and the joint can operate in the active control mode driven by electric power. When the DC servo motor is not powered, the joint 51 can be moved manually in the passive control mode. During both active and passive control modes, the movement of the joint 51 is monitored by the optical encoder 53, and the operator can switch freely between the active and passive modes.

Manipulation of the surgical robot in this example is governed by a surgical navigation system that includes two tracking devices that emit or reflect infrared signals. One tracking device 58 is mounted to the shoulder of the robot arm, i.e., at the location of the first revolute joint 21. This device tracks the position of the portion of the robot arm near the shoulder. A second tracking device 59 is mounted to the tool holder 35 to track the position of the surgical tool held in the holder. Together, these two tracking devices determine the position of the robot arm and operate in conjunction with navigation control to perform a fine adjustment of the position of the surgical tool.

Figure 5:
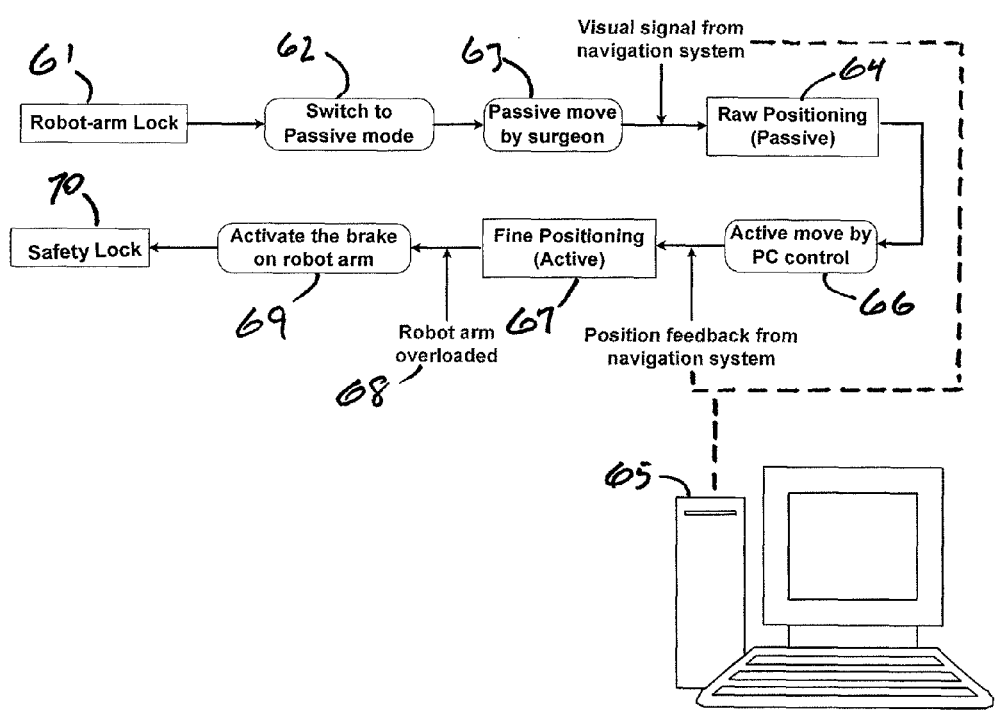
FIG. 5 is one example of a workflow chart for an active-passive hybrid control method according to the invention.

FIG. 5 is a workflow chart for an active-passive hybrid control method according to the present invention. The robot arm is initially in a locked position 61. When the robot is ready for use in surgery, the robot is switched 62 to the passive control mode 63, and in that mode the surgeon can manually move the robot arm to a rough position 64 that is near the final position, using either image-based or non-image-based guidance from the surgical navigation system 65. The robot is then switched to the active control mode 66, in which a fine adjustment 67 to the final position can be achieved using the position feedback from the surgical navigation system 65. If the robot becomes overloaded 68 in this mode, the electromagnetic brakes will be activated 69 to lock 70 the robot arm, preventing any further movement. This active-passive hybrid control method can shorten the operation time, minimize the range of auto-motion, increase safety, and also ensure the precision and accuracy of the surgical operation, all with the result of improving the utility and safety of the robot.

Initial positions of the surgical robot for different surgeries can be planned or pre-programmed before the operation begins. The robot will then automatically move to certain positions and orientations which are specialized to different surgery needs. This significantly decreases the setup time for the robot.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

We claim:

1. A surgical robot comprising a base and a tool holder adjustably connected to each other by way of a connection that comprises a series of at least seven joints with linking members in between,
    wherein the series of joints comprises:
        (1) a prismatic joint that connects the base to a vertically sliding block;
        (2) an arc-shaped sliding joint that connects the sliding block to an arc-shaped linking member; and
        (3) a robotic arm that comprises at least five motor-driven revolute joints, each of which is configurable with a hardware switch for automated operation under active control or for passive control by manual override;
    wherein the prismatic joint is constructed and arranged so as to adjust the height of the robotic arm; and
    wherein the arc-shaped sliding joint is constructed and arranged so as to move around the axis of a patient's body, thereby positioning the robotic arm for optimized performance within a specified workspace for a selected surgical procedure.

2. The surgical robot of claim 1 comprising a rotary joint governed by manual operation only situated between the arc-shaped linking member and the robotic arm,
    wherein the rotatory joint has a range of motion of at least 180 degrees.

3. The surgical robot of claim 2 further comprising a tracking device mounted to said rotary joint.

4. The surgical robot of claim 2 further comprising a first tracking device mounted to said rotary joint and a second tracking device mounted to said tool holder.

5. The surgical robot of claim 2 wherein said revolute joints are defined as first, second, third, fourth, and fifth revolute joints in succession, with said first revolute joint closest to the arc-shaped linking member,
    wherein said first and second revolute joints have axes of rotation that intersect with each other.

6. The surgical robot of claim 2 wherein said revolute joints are defined as first, second, third, fourth, and fifth revolute joints in succession, with said first revolute joint closest to the arc-shaped linking member,
    wherein said second and third revolute joints have axes of rotation that are parallel to each other.

7. The surgical robot of claim 2 wherein said revolute joints are defined as first, second, third, fourth, and fifth revolute joints in succession, with said first revolute joint closest to the arc-shaped linking member,
    wherein said third and fourth revolute joints have axes of rotation that intersect with each other.

8. The surgical robot of claim 2 wherein said revolute joints are defined as first, second, third, fourth, and fifth revolute joints in succession, with said first revolute joint closest to the arc-shaped linking member,
wherein said fourth and fifth revolute joints have axes of rotation that intersect with each other.

9. The surgical robot of claim 1 wherein said revolute joints are defined as first, second, third, fourth, and fifth revolute joints in succession, with said first revolute joint closest to the arc-shaped linking member,
wherein said first and second revolute joints have axes of rotation that intersect with each other.

10. The surgical robot of claim 1 wherein said revolute joints are defined as first, second, third, fourth, and fifth revolute joints in succession, with said first revolute joint closest to the arc-shaped linking member,
wherein said second and third revolute joints have axes of rotation that are parallel to each other.

11. The surgical robot of claim 1 wherein said revolute joints are defined as first, second, third, fourth, and fifth revolute joints in succession, with said first revolute joint closest to the arc-shaped linking member,
wherein said third and fourth revolute joints have axes of rotation that intersect with each other.

12. The surgical robot of claim 1 wherein said revolute joints are defined as first, second, third, fourth, and fifth revolute joints in succession, with said first revolute joint closest to the arc-shaped linking member,
wherein said fourth and fifth revolute joints have axes of rotation that intersect with each other.

13. The surgical robot of claim 1 wherein each of said motor-driven revolute joints comprises a DC servo motor having an output shaft, a revolute joint shaft linked to said output shaft by a coupling, an optical encoder arranged to monitor movement of said DC servo motor, a harmonic reducer coupled to said revolute joint shaft, and an electromagnetic brake arranged to engage said revolute joint shaft.

14. The surgical robot of claim 1 wherein said motor-driven revolute joints are driven by a DC motor and controller, and said surgical robot further comprises an electromagnetic brake arranged to lock said linking members upon overload detection by said DC motor controller.

15. A method for operating a surgical robot according to claim 1, said method comprising:
(a) mounting a surgical tool to the tool holder on said surgical robot;
(b) manually adjusting all of said joints to place said tool at a selected position; and
(c) once said tool is so placed, further adjusting said tool by motorized operation of the revolute joints in said robotic arm.

16. The method of claim 15 wherein step (b) is performed under visual guidance by a surgical navigation system.

17. The method of claim 15 wherein step (c) is performed under position feedback by a surgical navigation system.

18. A method of operating a surgical robot according to claim 1 to position a surgical tool for a specified surgical operation in a specified workspace, said method comprising:
(a) mounting said tool in the tool holder of said surgical robot;
(b) operating said surgical robot so that it positions the tool by automated navigation that is pre-programmed in accordance with said specified surgical operation and said specified workspace to achieve optimal performance of said operation in said workspace.

19. The method of claim 18 further comprising adjusting said tool further according to visual guidance from a surgical navigation system.

20. The method of claim 18 further comprising adjusting said tool further according to position feedback from a surgical navigation system.

* * * * *